(12) United States Patent
Nakagawa et al.

(10) Patent No.: US 7,527,692 B2
(45) Date of Patent: May 5, 2009

(54) PROCESSING APPARATUS WHICH PERFORMS PREDETERMINED PROCESSING WHILE SUPPLYING A PROCESSING LIQUID TO A SUBSTRATE

(75) Inventors: Yoshiyuki Nakagawa, Kyoto (JP); Kazuhiro Murata, Ibaraki-ken (JP)

(73) Assignees: National Institute of Advanced Industrial Science and Technology (JP); Dainippon Screen Mfg. Co., Ltd. (JP)

( * ) Notice: Subject to any disclaimer, the term of this patent is extended or adjusted under 35 U.S.C. 154(b) by 766 days.

(21) Appl. No.: 11/086,969

(22) Filed: Mar. 22, 2005

(65) Prior Publication Data

US 2005/0212837 A1    Sep. 29, 2005

(30) Foreign Application Priority Data

Mar. 23, 2004    (JP)    ............................. 2004-083961

(51) Int. Cl.
*B05B 7/06* (2006.01)
*B05B 3/00* (2006.01)
*B05B 5/025* (2006.01)
*B05C 11/00* (2006.01)

(52) U.S. Cl. .................... 118/313; 118/631; 118/323; 118/712; 239/706

(58) Field of Classification Search ......... 118/313–316, 118/669, 681, 712, 713, 620, 621, 629–631, 118/323; 347/8, 19, 20, 40; 422/100–104; 427/457, 458, 475, 483, 485, 486; 239/698, 239/692, 701–704, 690, 697; 96/27, 53; 435/285.2, 285.3

See application file for complete search history.

(56) References Cited

U.S. PATENT DOCUMENTS

| 6,474,573 | B1 * | 11/2002 | Kelly .......................... 239/690 |
| 6,776,844 | B2 * | 8/2004 | Yonekura et al. ............. 118/621 |
| 6,933,958 | B2 * | 8/2005 | Nakamura et al. .......... 347/256 |

(Continued)

FOREIGN PATENT DOCUMENTS

| JP | 11-285661 | 10/1999 |
| JP | 2003-112098 | 4/2003 |
| JP | 2004-165587 | 6/2004 |

OTHER PUBLICATIONS

** EP 1 477 230 A1, published Nov. 2004 corresponds to the above Japanese patent.

*Primary Examiner*—Yewebdar T Tadesse

(57) ABSTRACT

Above a substrate holder 1, an ordinary fluid jet nozzle 2 which is capable of injecting drops of a solution having ordinary particle diameters, a fine fluid jet nozzle 3 which is capable of injecting drops of a solution having fine particle diameters which are smaller than the ordinary particle diameters, and a regular reflection laser displacement gauge 4 are disposed. These are attached on the same plate, thereby forming a head 10. The head 10 freely moves in directions X, Y and Z, as an X-axis drive portion 41, Y-axis drive portions 42 and 43 and a Z-axis drive portion 44 operate in accordance with operation commands received from a controller 50 which controls the apparatus as a whole. It is therefore possible to set the head 10 to a predetermined position on a substrate S which is held by the substrate holder 1. Thus, the respective nozzles supply the solutions to any desired positions the substrate S.

19 Claims, 12 Drawing Sheets

U.S. PATENT DOCUMENTS

2004/0004653 A1* 1/2004 Pryor et al. ................. 347/106
2004/0131758 A1* 7/2004 Jung et al. .................... 427/8
2004/0239721 A1* 12/2004 Usuda ........................ 347/40
2006/0144331 A1* 7/2006 Hanafusa et al. ............ 118/712

* cited by examiner

F I G. 1A
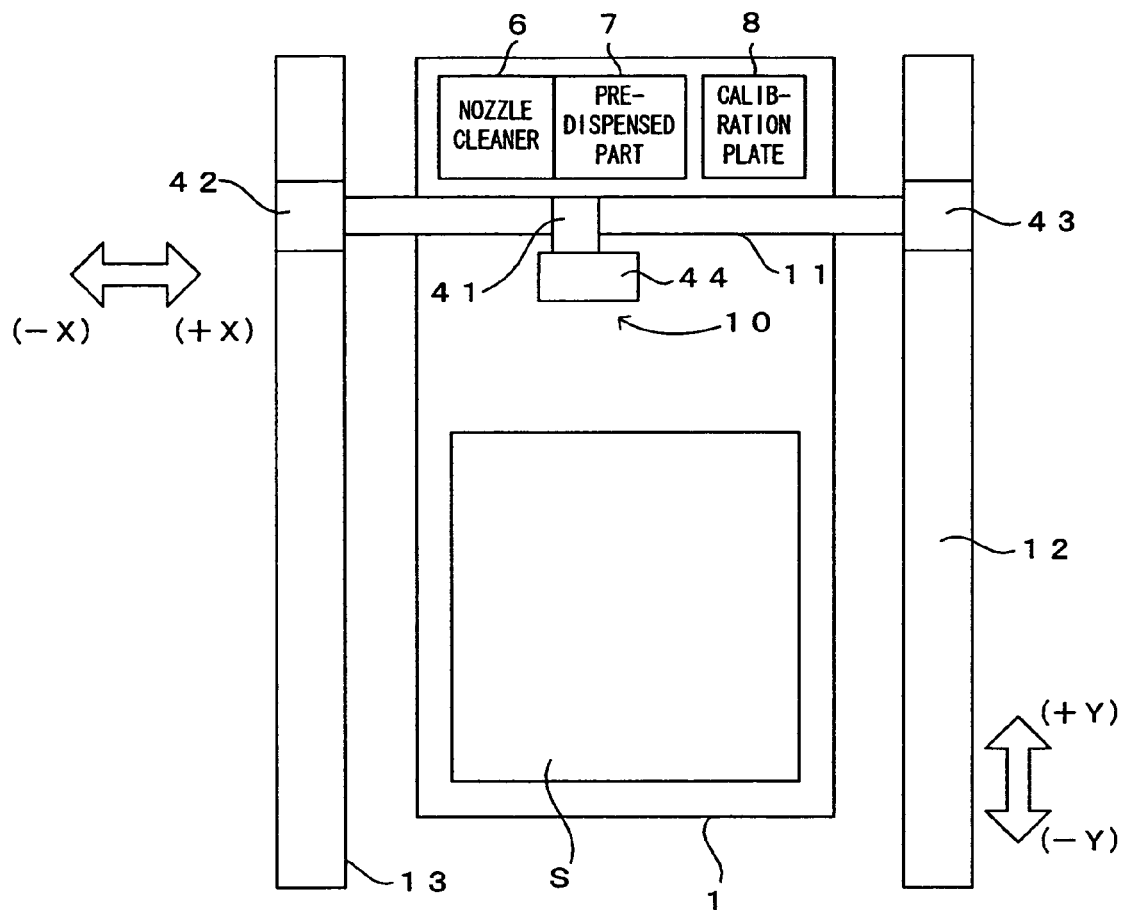
F I G. 1B
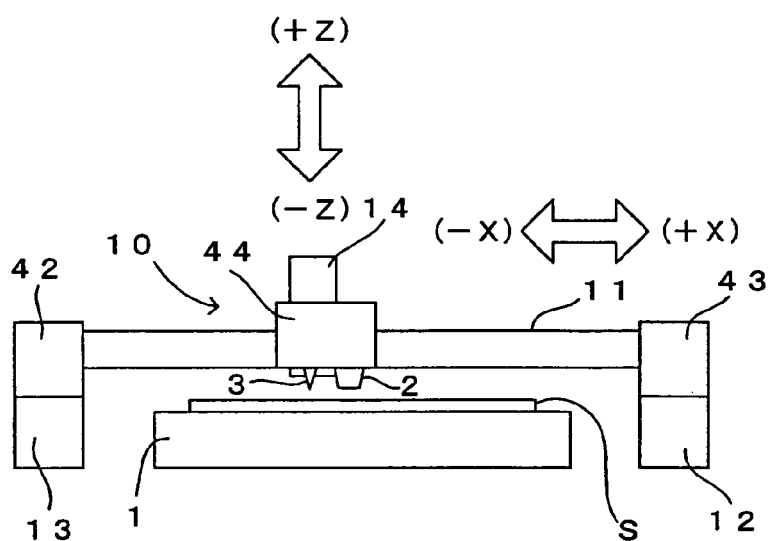

F I G. 5
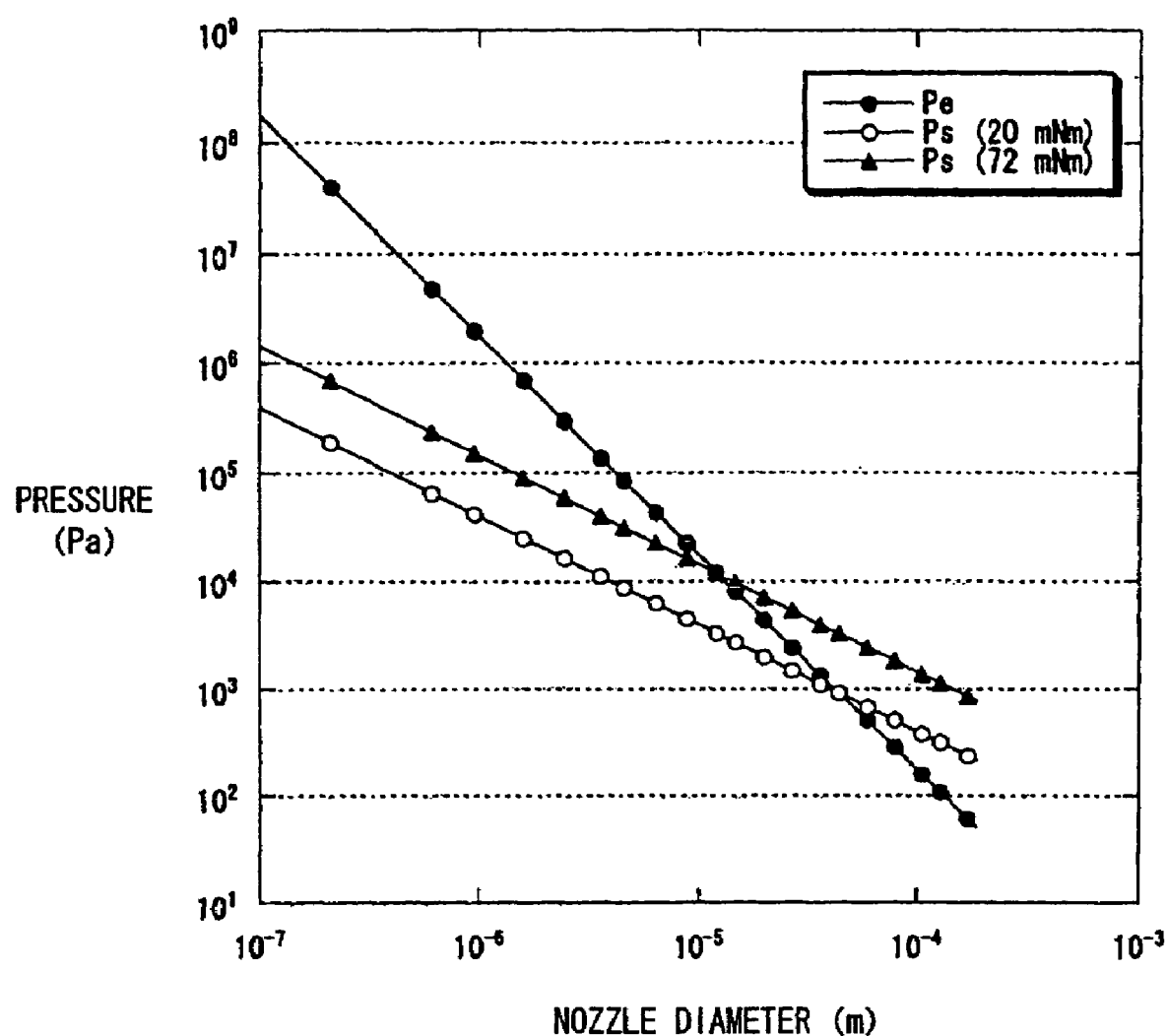

PROCESSING APPARATUS WHICH PERFORMS PREDETERMINED PROCESSING WHILE SUPPLYING A PROCESSING LIQUID TO A SUBSTRATE

CROSS REFERENCE TO RELATED APPLICATION

The disclosure of Japanese Patent Applications No. 2004-083961 filed Mar. 23, 2004 including specification, drawings and claims is incorporated herein by reference in its entirety.

BACKGROUND OF THE INVENTION

1. Field of the Invention

The present invention relates to a processing apparatus which performs, while supplying a processing liquid, predetermined processing of various types of substrates (hereinafter referred to simply as "substrates") which are used in apparatuses for manufacturing semiconductors and FPDs (Flat Panel Displays), printed substrate manufacturing apparatuses, apparatuses related to biology (for creating DNA micro arrays, DNA chips, etc.), chemical reaction test machines, etc.

2. Description of the Related Art

Such conventional processing apparatuses of the ink jet method are known which perform predetermined processing, such as formation of patterns, while injecting processing liquids directly upon substrates using the ink jet techniques. For instance, the processing apparatus described in Japanese Patent Application Laid-Open Gazette No. 2003-112098 for example is an apparatus which forms a resist film while supplying a resist liquid as a processing liquid upon a substrate. In this apparatus, while an ink jet nozzle moves above a substrate in directions X and Y, the nozzle injects the resist liquid, thereby forming a resist film at a desired position on the substrate.

SUMMARY OF THE INVENTION

By the way, using an ink jet nozzle as that described above in the following manner has been proposed. According to this proposed technique, drops of a solder paste are injected directly toward a substrate instead of injecting a resist liquid, and a wiring pattern is formed. When the proposed technique is used, since a wiring pattern is formed directly on a substrate, wiring can be formed efficiently. Meanwhile, although it is increasingly necessary that the diameter of an injection outlet of a nozzle is small as wiring patterns become finer and finer these days, clogging of the nozzle is arising as a big problem. In addition, to the extent that an ink jet nozzle is used, the injection capability is limited. This inevitably reduces the particle diameter of a drop which an ink jet nozzle can stably inject down into a predetermined range. Owing to this, in the case of an apparatus which performs predetermined processing while supplying drops of processing liquid upon a substrate by the ink jet method, drops can be supplied only to a region which is as wide as or wider than the particle diameters of the drops, thus limiting substrates which can be processed.

Further, since the particle diameters of drops are fixed in the conventional apparatus, even when a processing liquid is to be supplied to a region which is sufficiently wider than the particle diameters of drops, the amount of drops injected and supplied from the nozzle to a substrate per unit time is restricted to values which correspond to the particle diameters of drops (i.e., the minimum amount), which serves as a major obstacle against an improvement of the throughput.

Further, although regions of different sizes which are to receive a processing liquid are present even within a single substrate in some cases, that is, there are some substrates which include both fine regions and other regions which are wider than the fine regions, an apparatus as that described above which fixes the particle diameters of drops has difficulty in flexibly adapting to such a substrate. In other words, when there is only one type of particle diameters of drops of a processing liquid, it is necessary to reduce the particle diameter of drops of the processing liquid in order to supply the processing liquid to a fine region, and this however results in supplying the processing liquid at the small particle diameter even to other regions which are wider than fine regions, whereby the throughput inevitably decreases. Further, when a substrate includes a smaller processing region than the particle diameter of drops of the processing liquid, it is not possible to process this region. In the case of the conventional ink jet method (the piezo method or the thermal method) in particular, it is difficult to inject a drop of an extremely small amount below 1 pl (pico liter). This is because the finer a nozzle becomes, the larger the necessary pressure for injection becomes.

While this has given rise to a demand for an apparatus which is capable of supplying a processing liquid to a substrate as drops which have diameters suitable to a region within the substrate which is to receive the processing liquid, there still is a problem today that the particle diameters of drops are generally fixed and an apparatus is not versatile as described above. Although there are some apparatuses of the piezo method which can change the particle diameters of drops to a certain extent at the same nozzle diameter, basically, it can be said that the particle diameters of drops are generally fixed by the diameter of a nozzle.

A primary object of the present invention is to provide a processing apparatus which is highly versatile and capable of performing predetermined processing at a high throughput.

To achieve the object above, the present invention is directed to a processing apparatus which performs predetermined processing while supplying a processing liquid to a substrate, comprising: a substrate holder which holds the substrate; an ordinary fluid jet unit which injects drops of the processing liquid having ordinary particle diameters toward the substrate; a fine fluid jet unit which injects drops of the processing liquid having fine particle diameters which are smaller than ordinary particle diameters toward the substrate; a driving device which moves each one of the ordinary fluid jet unit and the fine fluid jet unit relative to the substrate which is held by the substrate holder; and a controller which adjusts the positions of each jet unit relative to the substrate and accordingly controls a feeding position of the drops.

With such a structure according to the present invention, an ordinary fluid jet unit which injects drops of a processing liquid having ordinary particle diameters, and a fine fluid jet unit which injects drops of the processing liquid having fine particle diameters which are smaller than the ordinary particle diameters, are disposed within one apparatus. Further, each jet unit is moved relative to a substrate and a feeding position at which each jet unit injects drops is accordingly controlled. It is thus possible for each jet unit to inject drops having different particle diameters from the other in accordance with a processing region on the substrate, which is highly versatile. For instance, the fine fluid jet unit may supply the processing liquid upon the substrate when a fine region on the substrate is to receive the processing liquid and the ordinary fluid jet unit may supply the processing liquid upon the substrate for a processing region which is wider than a fine region (a region other than a fine region), thereby improving the throughput.

Such an ordinary fluid jet unit may be an ink jet nozzle of the piezo (piezo-electric element) type or the thermal types (bubble jet; registered trademark) both of which have been put to practical use and widely used. The former, utilizing expansion and contraction of a piezo-electric element disposed to a nozzle body under an applied voltage, pressurizes a processing liquid held inside the nozzle body and injects drops of the processing liquid. The latter, heating the processing liquid by means of a heater disposed to the nozzle body and creating bubbles in the processing liquid, pressurizes the processing liquid held inside the nozzle body and injects drops of the processing liquid. The both types apply pressure upon the processing liquid held inside the nozzle body and makes drops of the processing liquid injected through an ordinary outlet formed at the tip of the nozzle body. However, with these types, it is difficult to inject drops in an extremely small amount as that less than 1 pl (one picoliter). The reason is because the smaller the nozzle and the particle diameters are, the larger the capillary effect becomes than the force of injection which develops owing to the inertia force of the mass of the drops and more difficult it becomes to inject.

In the meantime, used as the fine fluid jet unit is a nozzle which, based on a totally different principle from that of the other type described above, is capable of injecting drops in an extremely small amount which has been heretofore impossible. In this nozzle, an electrode contacting the processing liquid held inside the nozzle body charges up the processing liquid which is near a fine outlet formed at the tip of the nozzle body, an electric field is locally created in the vicinity of the fine outlet, and drops of the processing liquid are injected through the fine outlet. To be more specific, drops of the processing liquid are injected due to electrostatic sucking force which acts between the electric charges of the charged processing liquid and mirror charges induced by these electric charges to symmetric positions with respect to the substrate. Utilizing such a structure, it is possible to inject drops in 1 fl (one femtoliter) or less.

The processing liquid used in the present invention may be a nano-paste (available from Harima Chemicals, Inc.) in which silver particles are dispersed within a solvent, a gold nano-paste, or an equivalent colloid solution of fine metal particles. Using these, it is possible to form a fine metal pattern whose line width is a few μm on a substrate. Meanwhile, when a soluble derivative of conductive polymers is used as the processing liquid, it is possible to form fine patterns for organic EL elements. The soluble derivative of conductive polymers may be MEH-PPV (polyparaphynylenevinylene) for instance. Alternatively, the processing liquid may be a catalytic solution or the like which is prepared by dispersing ultra-fine particles of transition metal such as iron, cobalt and nickel in an organic solvent.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

BRIEF DESCRIPTION OF THE DRAWINGS

FIG. 1a and FIG. 1b are drawings which show a first preferred embodiment of a processing apparatus according to the present invention;

FIG. 5 is a drawing which shows a result of modeling of nozzle diameter dependency of surface tension and an electrostatic pressure in the case of a fine fluid jet nozzle;

DETAILED DESCRIPTION OF THE PREFERRED EMBODIMENTS

First Embodiment (Forming Fine Line)

Figure 2:
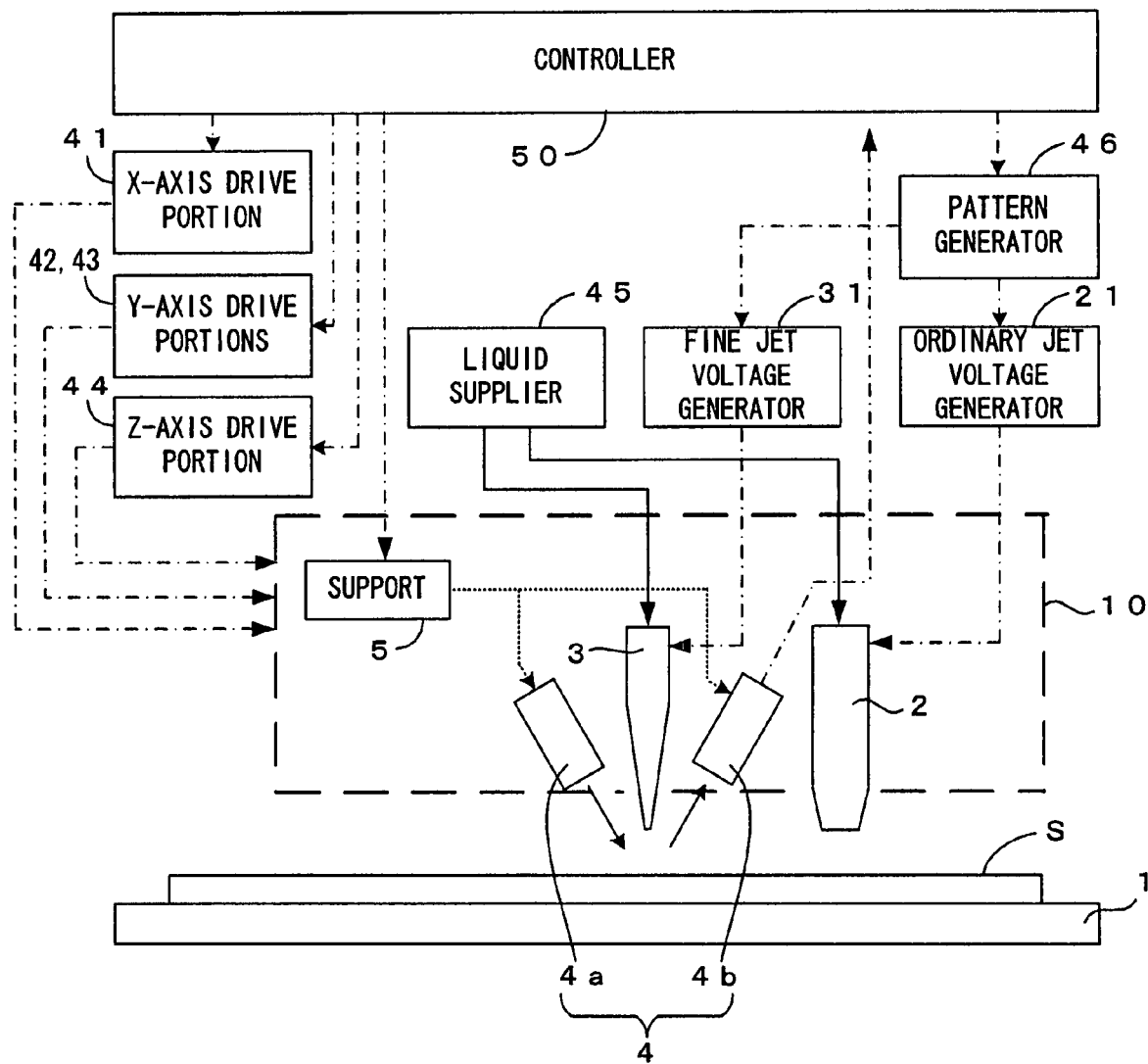
FIG. 2 is a schematic drawing which shows the electric structure of the processing apparatus of FIG. 1.

FIG. 1 is a drawing which shows a first embodiment of a processing apparatus according to the present invention. FIG. 2 is a schematic drawing which shows the electric structure of the processing apparatus of FIG. 1. This processing apparatus is a processing apparatus which forms a predetermined pattern while supplying a metal paste, a colloid solution of fine metal particles or the like (hereinafter referred to simply as a "solution") as the "processing liquid" of the present invention to a substrate S which is an object-to-be-processed. In this processing apparatus, a substrate holder 1 holds the substrate S, and by means of vacuum suction from a suction groove (not shown) which is formed on the substrate holder 1, the substrate S is fixed. As the substrate holder, a stone faceplate can be used for example. In the first embodiment, the substrate holder 1 thus corresponds to the "substrate holding means."

Disposed above the substrate holder 1 are an ordinary fluid jet nozzle 2 which is capable of injecting a solution having ordinary particle diameters, a fine fluid jet nozzle 3 which is capable of injecting drops of a solution having fine particle diameters which are smaller than the ordinary particle diameters, and a regular reflection laser displacement gauge 4. These are attached on the same plate (not shown), thereby forming a head 10. As the ordinary fluid jet nozzle 2 and the fine fluid jet nozzle 3 are integrated with each other as one unit, it is not necessary to dispose one drive means for each nozzle and it is therefore possible to simplify the structure of the apparatus. It is further possible to enhance the accuracy of the position of the ordinary fluid jet nozzle 2 relative to the position of the fine fluid jet nozzle 3. More than one ordinary fluid jet nozzles 2 and more than one fine fluid jet nozzles 3 may be attached to the head 10 (multi-channel structure) instead of using only one ordinary fluid jet nozzle 2 and only one fine fluid jet nozzle 3. This improves the throughput of the apparatus. Where multiple nozzles are to be disposed, processing such as formation of a pattern is performed through raster scanning. In short, the head 10 scans the entire area on the substrate S while ejection of the solution at each nozzle is ON/OFF-controlled, whereby the solution is supplied to a desired region on the substrate S.

An X-axis drive portion 41 which moves the head 10 in a direction X along a guide rail 11 is connected to the head 10. On the both ends of the guide rail 11, there are Y-axis drive portions 42 and 43 which move the guide rail 11 in a direction Y The guide rail 11 moves in the direction Y on paired guide rails 12 and 13 which are disposed on the both sides in the direction X to the substrate holder 1, when the Y-axis drive portions 42 and 43 are driven in synchronization to each other. Further disposed to the head 10 is a Z-axis drive portion 44 which moves the head 10 along a guide rail 14 which is formed along a side surface of the X-axis drive portion 41 (Z-axis direction). As the respective drive portions, drive mechanisms such as motors may be used, whereas screw mechanisms using ball screws or other known mechanisms of various types may be used as the respective guide rails. As the X-axis drive portion 41, the Y-axis drive portions 42 and 43 and the Z-axis drive portion 44 operate in accordance with operation commands from a controller 50 which controls the apparatus as a whole, the head 10 freely moves in the directions X, Y and Z. This sets the head 10 to any desired position on the substrate S which is held by the substrate holder 1.

As shown in FIG. 2, the ordinary fluid jet nozzle 2 and the fine fluid jet nozzle 3 are connected via pipes with a liquid supplier 45 serving as a source from which the solution is supplied, so that the solution fed under pressure from the liquid supplier 45 is held inside each nozzle. The ordinary fluid jet nozzle 2 is connected further with an ordinary jet voltage generator 21, and when under a predetermined voltage applied from the ordinary jet voltage generator 21, the ordinary fluid jet nozzle 2 injects the solution toward the substrate S. In a similar manner, the fine fluid jet nozzle 3 is connected with a fine jet voltage generator 31, and when under a predetermined voltage applied from the fine jet voltage generator 31, the fine fluid jet nozzle 3 injects the solution toward the substrate S. The structures and operations of the ordinary fluid jet nozzle 2 and the fine fluid jet nozzle 3 will be described in detail later.

Further, the ordinary jet voltage generator 21 and the fine jet voltage generator 31 are electrically connected with a pattern generator 46. Upon receipt of a pattern formation signal from the pattern generator 46, the ordinary jet voltage generator 21 and the fine jet voltage generator 31 apply the predetermined voltages respectively upon the ordinary fluid jet nozzle 2 and the fine fluid jet nozzle 3 for injection. The pattern formation signal gives a voltage generation command to the ordinary jet voltage generator 21 or the fine jet voltage generator 31 so that a predetermined pattern will be formed at a desired position on the substrate S. For instance, when receiving a signal representing a position on the substrate S from the controller 50, the pattern generator 46 outputs the pattern formation signal to the ordinary jet voltage generator 21 or the fine jet voltage generator 31 in accordance with this position signal. When the fine jet voltage generator 31 receives the pattern formation signal for instance, the fine jet voltage generator 31 applies the predetermined voltage upon the fine fluid jet nozzle 3. This makes the fine fluid jet nozzle 3 supply the solution to a predetermined position on the substrate S. In a similar fashion, when the ordinary jet voltage generator 21 receives the pattern formation signal, the ordinary fluid jet nozzle 2 supplies the solution to a predetermined position on the substrate S. Because of the solution supplied from the ordinary fluid jet nozzle 2 or the fine fluid jet nozzle 3, a pattern is formed at the predetermined position on the substrate S.

The regular reflection laser displacement gauge 4 will now be described. The regular reflection laser displacement gauge 4 is disposed for the purpose of measuring a displacement of a gap between the head 10 and the substrate S. To measure a displacement of the gap between the fine fluid jet nozzle 3 and the substrate S in particular, the regular reflection laser displacement gauge 4 is disposed so that a detect position, namely, the focal point of a laser will be located near a feeding position on the substrate S at which the solution from the fine fluid jet nozzle 3 is received. The regular reflection laser displacement gauge 4 comprises a light projector 4a which projects the laser toward the substrate S and a light receiver 4b which receives reflected laser light reflected from the substrate S. This achieves non-contact detection of a displacement of the gap between the head 10 and the substrate S. A support 5 supports the regular reflection laser displacement gauge 4, and as the support 5 moves, the detect position of the regular reflection laser displacement gauge 4 is varied. While reflection at the back surface of the substrate S may sometimes be a problem to the regular reflection laser displacement gauge 4, use of the regular reflection laser displacement gauge 4 of the CCD method in a detector solves this problem. In this case, since the profile of a detection beam will show two peaks corresponding to the front surface and the back surface, the peak corresponding to the back surface may be detected by means of software out from the beam profile and excluded from calculation of the center of gravity which is used for calculating the position of the beam, whereby the influence of reflection at the back surface is eliminated.

The support 5 may be formed by a piezo-electric element for instance, in which case as the piezo-electric element expands and contracts, a position on the substrate S can be automatically adjusted. This permits setting the detect position of the regular reflection laser displacement gauge 4 to a position on the substrate S at which the solution from the fine fluid jet nozzle 3 is received or to a desired position near this feeding position. For example, it is possible to align the detect position of the regular reflection laser displacement gauge 4 to an unsupplied region which is starved with the solution and does not include the feeding position at which the solution is supplied onto the substrate S from the fine fluid jet nozzle 3. Thus, it is possible to avoid denaturation of the solution caused by incidence of the laser upon drops of the solution injected from the fine fluid jet nozzle 3, and further, detection of drops of the solution supplied onto the substrate S utilizing the laser prevents the inconvenience of an error made by the displacement gauge. It is therefore possible to continuously detect a displacement of the gap between the fine fluid jet nozzle 3 and the substrate S. The gap between the fine fluid jet nozzle 3 and the substrate S is thus always accurately kept to a predetermined value.

Alternatively, the detect position of the regular reflection laser displacement gauge 4 may be aligned to an area in the vicinity including the feeding position at which the solution is supplied onto the substrate S from the fine fluid jet nozzle 3. In this case, after detection at a position where supply of the solution is planned prior to supply of the solution onto the substrate S from the fine fluid jet nozzle 3, the detection may be stopped. This improves the processing speed than where the detection is conducted successively. The support 5 thus corresponds to the "position adjusting mechanism" in the first embodiment.

In the event that a multi-nozzle (multi-channel) structure is used which uses linearly arranged heads or heads which are arranged in a two-dimensional arrangement, displacement information available at one place is insufficient, and hence, more than one regular reflection laser displacement gauges 4 may be mounted and an average of plural displacement signals from these displacement gauges may be used, or the freedom of the Z-axis drive portion 44 may be enhanced for line correction or surface correction.

Figure 3:
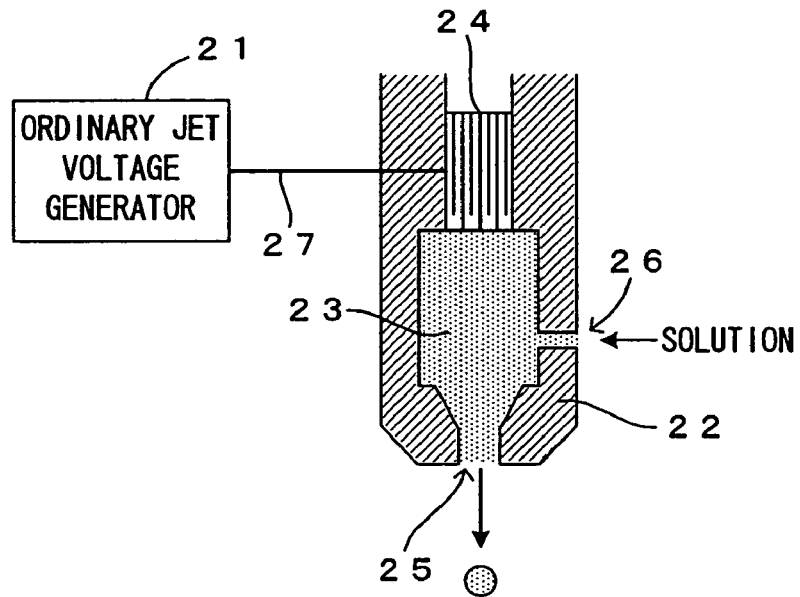
FIG. 3 is a side cross sectional view of an ordinary fluid jet nozzle.

FIG. 3 is a drawing which shows the structure of the ordinary fluid jet nozzle 2. A known piezo-type ink jet nozzle is used as the ordinary fluid jet nozzle 2 for instance. The ordinary fluid jet nozzle 2 comprises a nozzle body 22 containing a reservoir space 23 where it is possible to hold the solution, and a piezo-electric element 24 which is for pressurizing the solution inside the reservoir space 23. A bottom portion of the nozzle body 22 has an ordinary outlet 25 having an ordinary diameter (a diameter larger than 25 μm for example) at which the solution inside the reservoir space 23 is injected toward the substrate S. In addition, a feeding inlet 26 through which the solution is supplied into the reservoir space 23 is formed in a side surface of the nozzle body 22 and linked to the liquid supplier 45. The piezo-electric element 24 is electrically connected with the ordinary jet voltage generator 21 via a wire 27. Since the piezo-electric element 24 expands and contracts when applied with a voltage, when the ordinary jet voltage generator 21 applies the predetermined voltage upon the piezo-electric element 24, the piezo-electric element 24 expands and contracts and the solution held inside the reservoir space 23 is pressurized. As a result, drops of the solution are injected toward the substrate S through the ordinary outlet 25. The piezo-electric element 24 thus corresponds to the "pressure applying device" in the first embodiment.

The ordinary fluid jet nozzle 2 is not limited to a piezo-type ink jet nozzle but may be a known thermal-type (bubble jet type; registered trademark) ink jet nozzle. In the event that a thermal-type ink jet nozzle is used, the piezo-electric element 24 is replaced with heating means such as a heat generator which heats up the solution inside the nozzle, to thereby heat the solution and create bubbles in the solution. This pressurizes the solution, and drops of the solution are injected toward the substrate S through the ordinary outlet 25.

Figure 4:
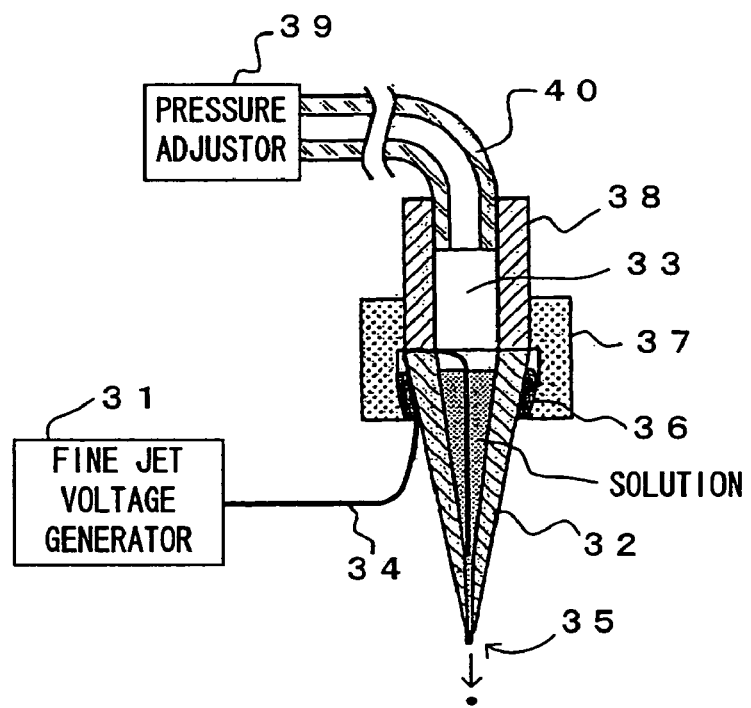
FIG. 4 is a side cross sectional view of a fine fluid jet nozzle.

FIG. 4 is a drawing which shows the structure of the fine fluid jet nozzle 3. The fine fluid jet nozzle 3 comprises a nozzle body 32 containing a reservoir space 33 where it is possible to hold the solution, and an electrode 34 which contacts the solution inside the reservoir space 33. A bottom portion of the nozzle body 32 has a fine outlet 35 having a fine diameter which is smaller than the ordinary diameter (a diameter of a submicron through 25 μm for example) at which the solution inside the reservoir space 33 is injected toward the substrate S. The nozzle body 32 is attached to a holder 38 via a shield rubber 36 and a nozzle clamp 37, and has such a structure which prevents leakage of the pressure inside the nozzle body 32. A pressure adjustor 39 is for adjusting the pressure inside the nozzle body 32, and the pressure inside the nozzle body 32 is adjusted through a pressure tube 40. The pressure adjustor 39 is used for the purpose of adjustment of the conductance (which represents how easily the solution inside the nozzle flows) and for the purpose of filling up the reservoir space 33 with the solution, and elimination of clogging of the nozzle, instead for the purpose of applying a high pressure and pushing out the solution from the fine outlet 35. Considering the formability, glass is used for the nozzle body 32 and a metal wire (tungsten wire) is used for the electrode 34. Alternatively, the electrode may be formed by plating inside the nozzle. Meanwhile, when the nozzle body 32 is made of a conductive material, the top of the nozzle body 32 is coated with an insulation material.

An operation of dropping from the fine fluid jet nozzle 3 will now be described. The electrode 34 is connected with the fine jet voltage generator 31, and therefore, the voltage generated by the fine jet voltage generator 31 is transmitted to the electrode 34, charges up the solution which is near the fine outlet 35 and develops a local electric field (the effect of electric field concentration) in the vicinity of the fine outlet 35. Electric charges Q concentrated on the fine outlet 35 guide mirror image charges Q', whose electric charge amounts are equivalent and polarity is the opposite, to symmetrical positions which are centered around the substrate S and off toward inside the substrate S exactly by the gaps between the electric charges Q and the substrate S. Electrostatic force (mirror image force) which acts between the electric charges Q and the mirror image charges Q' makes drops of the solution injected toward the substrate S through the fine outlet 35. While a necessary injection condition is that the electrostatic force exceeds surface tension which acts upon the solution inside the nozzle, it has been clarified that the smaller the nozzle diameter is, the larger the effect of electric field concentration is, which is advantageous to injection as described later.

FIG. 5 shows a result of modeling based on a local electric field model. FIG. 5 is a drawing which shows a relationship between a nozzle diameter r, a pressure Ps due to surface tension and an electrostatic pressure Pe. The illustrated surface tension is that of water ($\gamma$=72 mNm) and that of an organic solvent ($\gamma$=20 mNm). It is thus suggested that use of a sufficiently small nozzle diameter makes the electrostatic pressure Pe exceed the pressure Ps due to surface tension. In other words, fine drops can be injected. It is therefore possible to stably inject fine drops, which has been heretofore impossible in an ink jet method because of the problem of nozzle clogging, etc.

As described above, injection of fine drops from the fine fluid jet nozzle 3 is characterized in utilizing the effect of electric field concentration near the fine outlet 35 and the effect of mirror image force induced in the substrate S which is faced with the fine fluid jet nozzle 3. Owing to this, it is not necessary to make the substrate S or the substrate holder 1 conductive or apply a voltage upon these. In short, the substrate may be an insulating glass substrate, a plastic substrate of polyimide or the like, a ceramic substrate, a semiconductor substrate, etc.

The voltage applied upon the electrode 34 may be either positive or negative. In addition, with the gap between the fine fluid jet nozzle 3 and the substrate S kept at a few μm to a few hundreds of μm or shorter, injection of the solution is made even easier.

The apparatus will be described further, referring back to FIG. 1. A nozzle cleaner 6, a pre-dispensed part 7 and a calibration plate 8 are attached on the substrate holder 1. The nozzle cleaner 6 and the pre-dispensed part 7 are disposed for the purpose of cleaning the fine fluid jet nozzle 3. The nozzle cleaner 6 comprises a few types of containers for cleaning solvents and performs ultrasonic cleaning. For each solution to use, a cleaning solvent whose detergency is optimal is used, and after cleaning with thus selected cleaning solvent, cleaning with ethyl alcohol is executed. The cleaning solvent may be exchanged manually at regular intervals. This is because the amount of the solution adhering to the tip of the fine fluid jet nozzle 3 is extremely small and contamination of the solvent in the cleaning container is minor. A stainless steel tray is disposed to the pre-dispensed part 7, and initial injection is performed.

A glass plate for instance is used as the calibration plate 8, and before forming a pattern, the positions of the ordinary fluid jet nozzle 2 and the fine fluid jet nozzle 3 are aligned to each other on the glass plate. The procedure of this is as follows. First, with the solution injected from the fine fluid jet nozzle 3, a cross mark is formed on the glass plate. The ordinary fluid jet nozzle 2 then injects the solution, thereby similarly forming a cross mark on the glass plate. A position correction value is calculated while visually inspecting a displacement of the respective cross marks relative to each other with a microscope (not shown). Thus calculated position correction value is fed to the controller 50, whereby the position of the ordinary fluid jet nozzle 2 and the position of the fine fluid jet nozzle 3 are aligned relative to each other.

Figure 6:
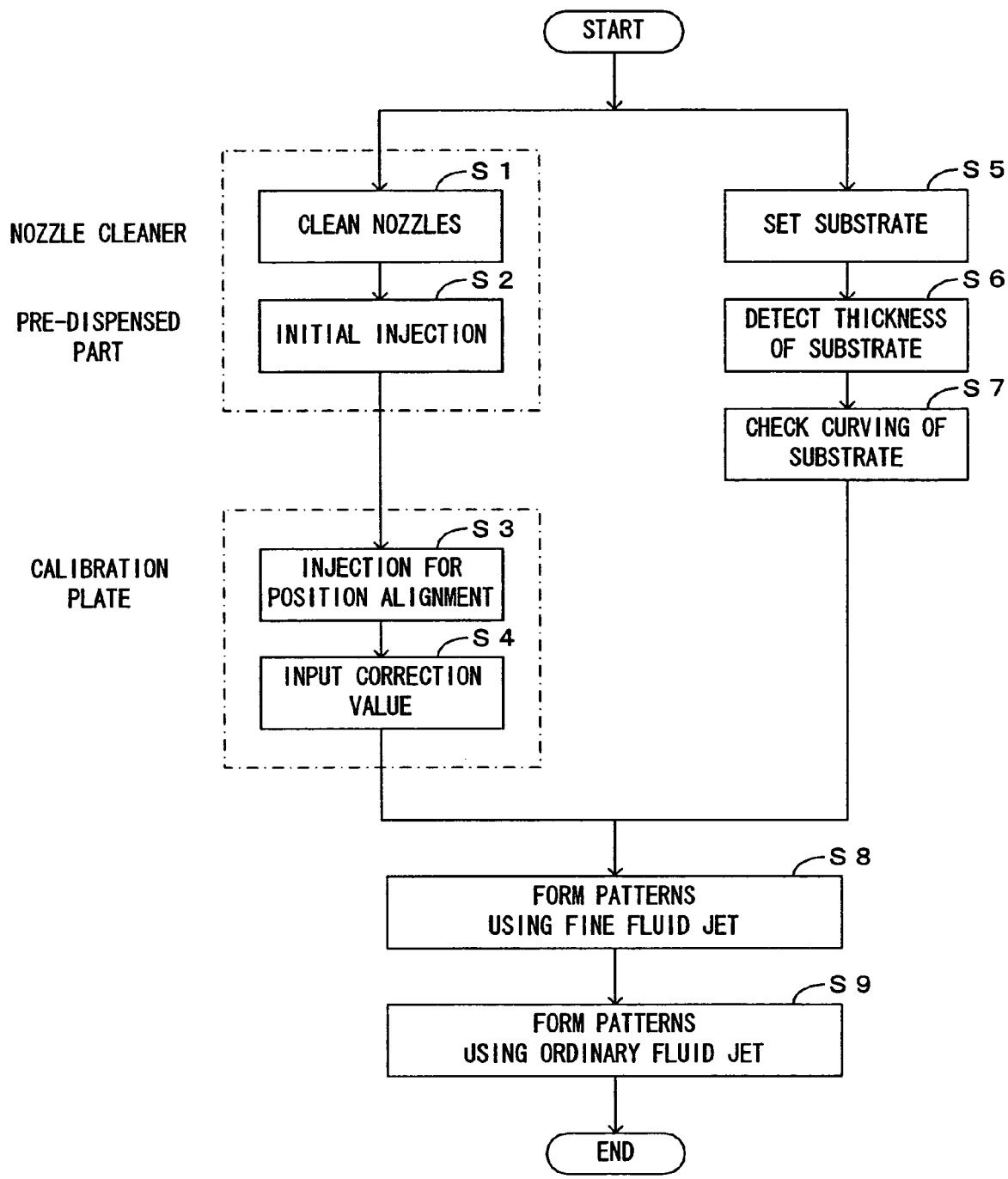
FIG. 6 is a flow chart which shows one example of an operation of the processing apparatus of FIG. 1.

One example of the operation of the processing apparatus having the structure above will now be described with reference to FIG. 6. FIG. 6 is a flow chart which shows the operation of the processing apparatus of FIG. 1. Formation of a wiring pattern to mount integrated circuit components of an LSI device or the like on the substrate S will be described.

First, as preparation for injection, in the nozzle cleaner 6, the ordinary fluid jet nozzle 2 and the fine fluid jet nozzle 3 are each cleaned (Step S1). The solution is then fed under pressure to each nozzle from the liquid supplier 45, and in the pre-dispensed part 7, each nozzle injects the solution, thereby performing initial injection (Step S2). This completes cleaning of each nozzle. Next, with each nozzle injecting the solution, position aligning patterns are formed on the calibration plate 8 (Step S3). The position correction value is calculated while visually confirming a displacement of thus formed patterns relative to each other with a microscope, and this correction value is input to the controller 50 (Step S4). This completes aligning of the position of the ordinary fluid jet nozzle 2 relative to the position of the fine fluid jet nozzle 3. Meanwhile, as preparation of the substrate S, the substrate S is set to the substrate holder 1 and the substrate S is vacuum-sucked (Step S5). Following this, with the head 10 driven, the regular reflection laser displacement gauge 4 detects the thickness of the substrate S (Step S6) and curving of the substrate S is checked (Step S7).

When the preparation before forming a pattern is finished, first, pattern formation using the fine fluid jet nozzle 3 is executed (Step S8). The head 10 is set to a predetermined position on the substrate S, and drops having the fine particle diameters are supplied upon the substrate S from the fine fluid jet nozzle 3. In consequence, fine patterns having fine widths (e.g., patterns whose line widths are narrower than 25 μm) for peripheral sections of integrated circuit components of a device or the like are formed. Pattern formation using the ordinary fluid jet nozzle 2 is executed after pattern formation using the fine fluid jet nozzle 3 has completed (Step S9). The head 10 is set to a predetermined position on the substrate S, drops having ordinary particle diameters larger than fine particle diameters are supplied upon the substrate S from the ordinary fluid jet nozzle 2. As a result, ordinary patterns having ordinary widths which are wider than fine widths (patterns other than fine patterns, such as patterns whose line widths are wider than 25 μm) are formed. The ordinary patterns are formed after forming the fine patterns, to thereby prevent the patterns formed out of the drops having the ordinary particle diameters from interfering with the fine fluid jet nozzle 3. Of course, where such interference will not be a problem, fine patterns may be formed (Step S8) after forming ordinary patterns (Step S9).

Figure 7:
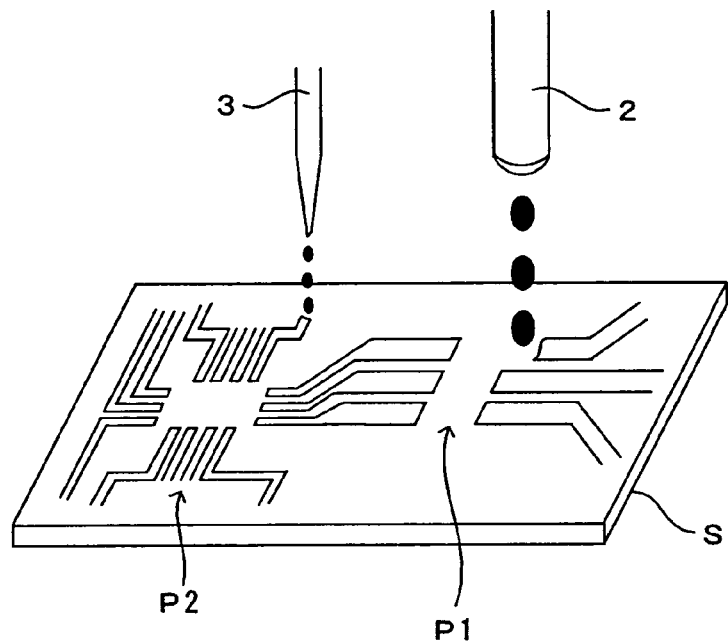
FIG. 7 is a drawing which shows how patterns including fine lines are formed.

FIG. 7 is a drawing which shows how patterns including fine lines are formed. To be more specific, FIG. 7 shows how wiring patterns are formed while injecting drops of a metal paste or the like toward the substrate S which is a glass epoxy substrate or a flexible printed substrate. Patterns P2 are wiring patterns which serve as a contact with a device and surrounding sections and which have fine widths, and these patterns are formed as drops having the fine particle diameters are supplied upon the substrate S from the fine fluid jet nozzle 3. Meanwhile, patterns P1 are ordinary patterns (i.e., patterns other than fine patterns) which are wider than fine widths, and these patterns are formed as drops having the ordinary particle diameters are supplied upon the substrate S from the ordinary fluid jet nozzle 2.

As described above, as for fine regions, the solution is supplied upon the substrate S from the fine fluid jet nozzle 3, thereby making wiring patterns fine, whereas as for wide regions which are wider than the fine regions (regions other than the fine regions), the solution is supplied upon the substrate S from the ordinary fluid jet nozzle 2, thereby improving the throughput. In other words, the particle diameters of drops need be small to form patterns of fine regions when there is only one type of particle diameters of drops, and when patterns are formed at this small diameter in wide regions which are wider than fine regions, the throughput decreases. In the first embodiment, the particle diameters of drops are changed in accordance with the widths of patterns to form, and hence, a deterioration of the throughput is prevented. Further, since the solution can be injected as drops having different particle diameters, it is possible to flexibly deal with a substrate in which a processing region is formed by fine regions, a substrate in which a processing region is formed by a wide region which is wider than a fine region and a substrate which includes the both regions, thus attaining high versatility. Use of the fine fluid jet nozzle 3 in particular realizes injection of drops having such particle diameters which could not have heretofore been stably injected owing to the problem of nozzle clogging and the like in the case of an ink jet nozzle, and therefore, there is not restriction over an object which can be processed unlike in the case of an apparatus which is built considering only the ink jet method. Because of this, regardless of the method including lithography, patterns of connection with an LSI device and the like which must be highly dense and have many connection points can be formed directly on a substrate.

Although the first embodiment requires that a pattern including a fine line are formed on the substrate S, this is not limiting. The present invention further has the following applications for instance.

(Forming Through Electrode of Si)

Over the recent years, owing to a demand for a higher density of integration as that typically for a mobile telephone, the SIP (System In Package) technology has advanced. With this technology, various types of devices fabricated using substrates such as thin wafers are stacked, sealed into one package and accordingly systematized. As for wiring of the various types of devices, the devices are wire-bonded with each other using a wire bonding apparatus. However, three-dimensional wire bonding using a wire bonder takes an enormously long time for teaching during initial setting of the apparatus, and further, has a problem with throughput. As an approach noting this, through holes may be formed in the respective substrates, a through electrode of Si may be formed in the through holes and the substrates formed these may be stacked one atop the other, instead of wire bonding. For reduction of a signal delay between the respective substrates and for attaining a higher density, the through holes for the through electrode of Si need have fine diameters (which are few scores μm or smaller). Meanwhile, in peripheral sections of the substrates, a through electrode for supplying power to the respective substrates is often formed in through holes which have ordinary diameters.

Figure 8:
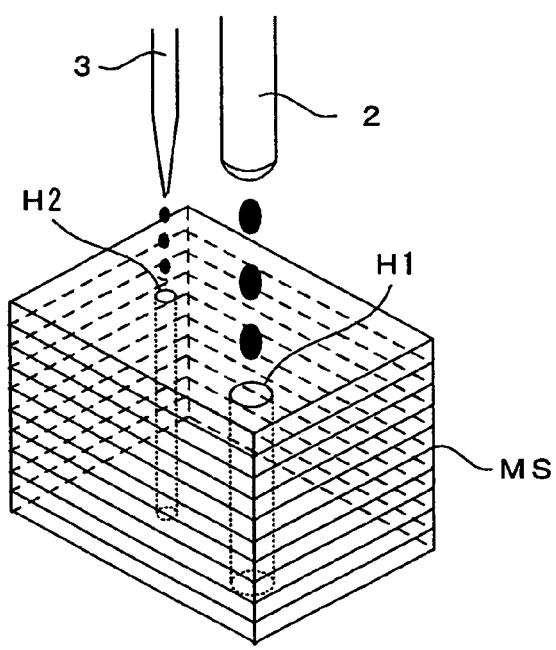
FIG. 8 is a drawing which shows how a through electrode of Si is formed.

FIG. 8 is a drawing which shows how the through electrode of Si is formed. To be more specific, FIG. 8 shows how a conductive solution such as a metal paste is supplied to through holes which are formed in a multi-layer substrate MS which is obtained by stacking the respective substrates which have the through holes, thereby filling up these through holes. Through holes H1 are through holes which have ordinary diameters, and as drops which have the ordinary particle diameters are injected from the ordinary fluid jet nozzle 2, the through holes are filled up. On the other hand, through holes H2 are through holes which have fine diameters which are smaller than the ordinary diameters, and as drops which have the fine particle diameters are injected from the fine fluid jet nozzle 3, these through holes are filled up.

As described above, since drops having the ordinary particle diameters or the fine particle diameters are supplied to the through holes in accordance with the diameters of the through holes, it is possible to improve the throughput. In short, the particle diameters of drops need be small to fill up through holes which have fine diameters in the event that there is only one type of particle diameters of drops, and when through holes larger than fine diameters are filled up with this small particle diameter, the throughput decreases. In the first embodiment, the particle diameters of drops are changed in accordance with the hole diameters, and hence, a deterioration of the throughput is prevented. Further, since the solution whose drops have different particle diameters can be injected, it is possible to supply drops whose particle diameters are suitable to the hole diameters, which is highly versatile. Use of the fine fluid jet nozzle 3 in particular realizes injection of drops having such particle diameters (which are few scores μm or smaller) which could not have heretofore been stably injected owing to insufficient accuracies at the time of impact, and therefore, there is not restriction over an object which can be processed unlike in the case of an apparatus which is built considering only the ink jet method. Still further, since the pattern shown in FIG. 7 are formed at the same time that the through electrode is formed, the versatility increases and the throughput is expected to further improve.

(Forming Solder Bumps)

Figure 9A:
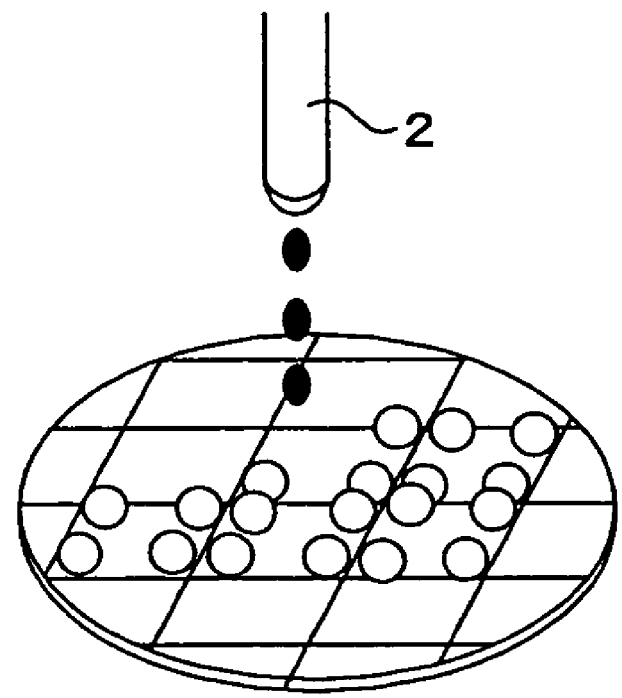
FIG. 9a and FIG. 9b are drawings which show how solder bumps are formed.
Figure 9B:
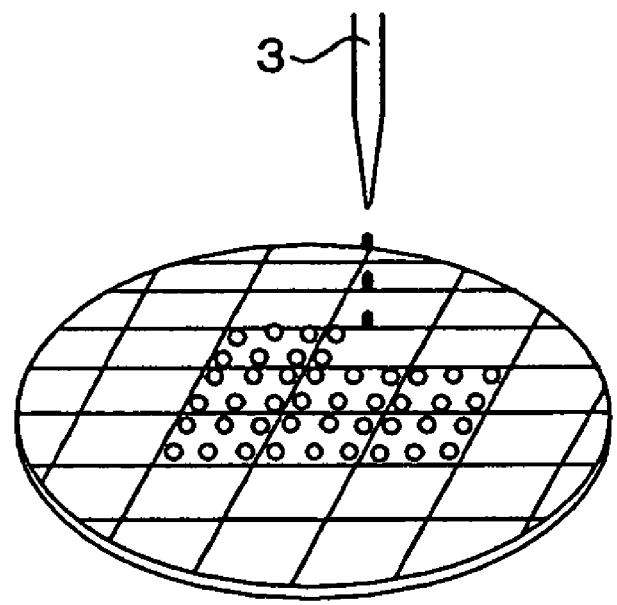

The invention is applicable also to formation of solder bumps. FIG. 9 is a drawing which shows how solder bumps are formed. In the section (a) in FIG. 9, bumps having ordinary diameters are formed as the ordinary fluid jet nozzle 2 injects drops which have the ordinary particle diameters. In the section (b) in FIG. 9, bumps having fine diameters which are smaller than the ordinary diameters are formed as the fine fluid jet nozzle 3 injects drops which have the fine particle diameters.

As described above, since drops which have the ordinary particle diameters or the fine particle diameters are supplied onto the substrate S in accordance with the diameters of bumps to form, it is possible to improve the throughput. In other words, the particle diameters of drops for forming bumps having fine diameters need be small diameters when there is only one type of particle diameters of drops, in the event that larger bump diameters than the fine diameters are to be attained with this small particle diameter, the amount of the liquid supplied to the substrate per unit time is restricted, ending up in a deterioration of the throughput. In the first embodiment, since the particle diameters of drops are changed in accordance with a bump diameter to attain, a deterioration of the throughput is prevented. Further, since the solution can be injected in drops having different particle diameters, it is possible to supply drops whose particle diameters are suitable to a bump diameter to the substrate, which is highly versatile. Use of the fine fluid jet nozzle 3 in particular realizes injection of drops having such particle diameters (It is said a limitation is one corresponding to the bump diameter of 30 μm.) which could not have heretofore been stably injected owing to insufficient accuracies at the time of impact, and therefore, it is possible to reduce bump diameters and there is no restriction over an object which can be processed unlike in the case of an apparatus which is built considering only the ink jet method.

Second Embodiment (Manufacturing DNA Microarray)

Figure 10:
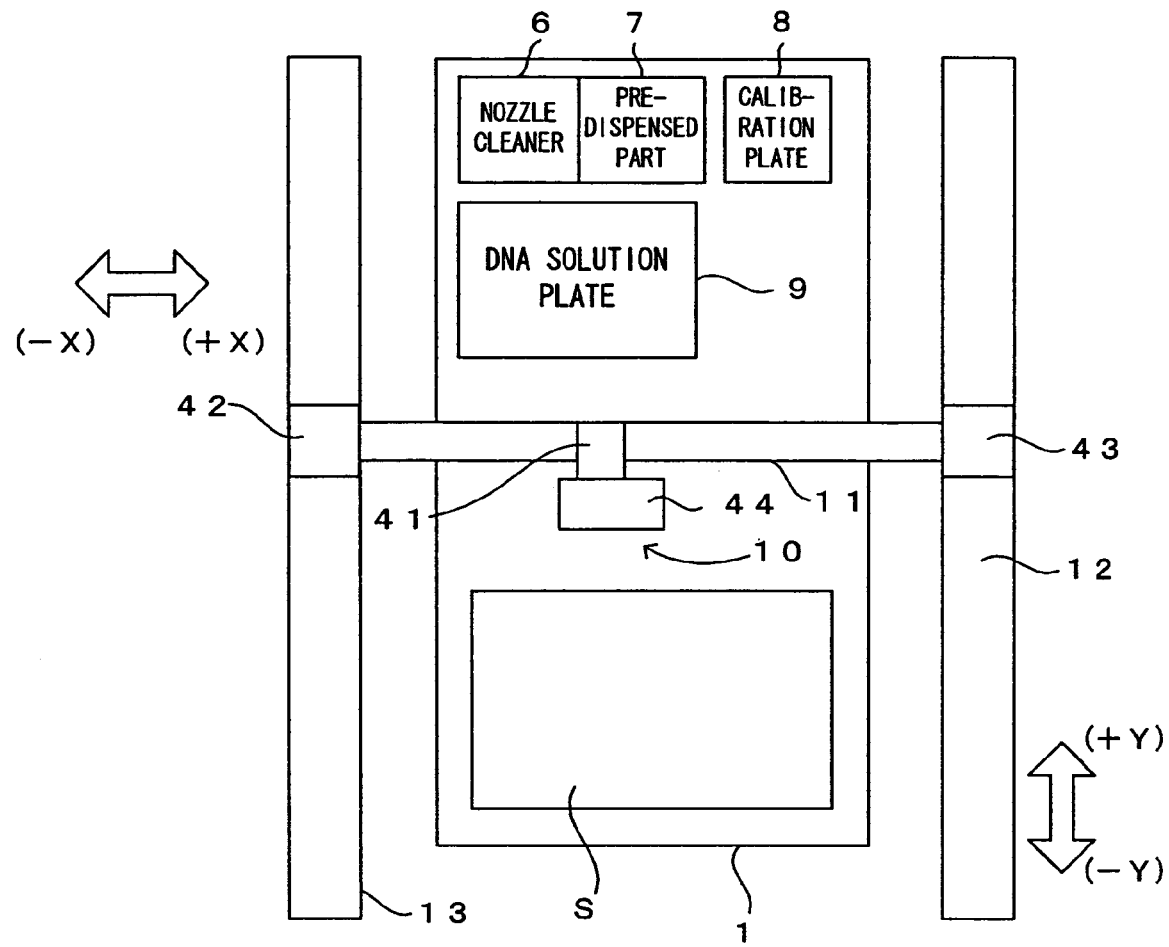
FIG. 10 is a drawing which shows a second preferred embodiment of the processing apparatus according to the present invention.

FIG. 10 is a drawing which shows the second preferred embodiment of the processing apparatus according to the present invention. This processing apparatus is a processing apparatus which manufactures a DNA micro array while supplying a probe DNA solution (hereinafter referred to as a "DNA solution") as the "processing liquid" of the present invention to the substrate S which is an object-to-be-processed. A slide glass or an Si wafer is used as the substrate S. Further, to increase the processing efficiency, plural substrates S are arranged on the substrate holder 1. For instance, 20×20 (total 400) substrates S are arranged.

A DNA micro array referred to here is what is obtained by arranging DNA fragments corresponding to genes of an organism to analyze at a high density as small spots on a substrate. For instance, DNAs taken from an organism are isolated and amplified by the PCR (Polymerase Chain Reaction) method, and DNA solutions are arranged on a substrate. It is said that there are 30000 through 40000 human genes and the number of DNA fragments corresponding to these is several tens of thousands, and therefore, several tens of thousands of types of DNA solutions are prepared.

A DNA micro array available from before is one that is obtained by arranging spots of about φ100 μm on a glass substrate which is about 10 mm times 10 mm using a spotter which comprises a needle of glass or metal which is stainless steel or the like. When these are to be arranged at the intervals of 100 μm, the number of spots can be maximum of 10000, leading to an inconvenience that a sufficient number of spots can not be ensured and plural glass substrates become necessary when the intended use is gene analysis on a large scale. For example, when the maximum number of spots per substrate is 10000, three to four glass substrate are necessary for analysis of human genes. In addition, there is a disadvantage that the diameters of spots are not uniform. While the diameters of spots are stable when the ink jet method is used, a reduction of the spot diameters necessitates a reduction of the diameter of the injection outlet of the nozzle, and stable injection is difficult due to clogging of the nozzle and other problems and because of a limitation of the injection capability of the nozzle. There is another problem as for how well the inside of the nozzle can be cleaned.

Although what is called a DNA chip is available in which a spot diameter of φ100 μm or smaller (φ23 μm for example) is realized using the lithographic techniques which are for fabrication of semiconductor devices, etc., these techniques impose a restriction over probe DNA solutions to mount and make it impossible to respond to various research needs. A spot diameter of φ100 μm or smaller leads to a problem that visual confirmation at the time of hybridization is difficult and that results of analysis are instable and the reproducibility is accordingly poor.

Figure 11:
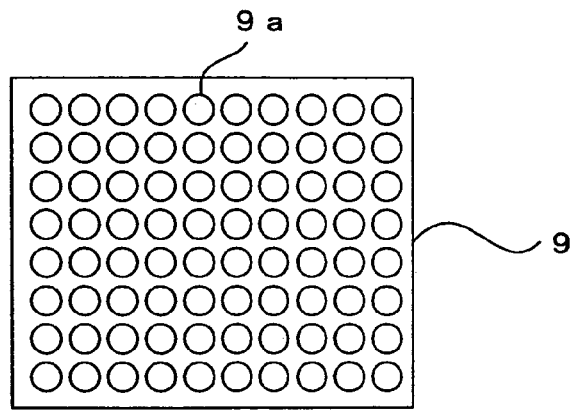
FIG. 11 is a drawing which shows the appearance of a DNA solution plate.

The apparatus will be described further, referring back to FIG. 10. A major difference of the second embodiment from the first embodiment is that a DNA solution plate 9 is disposed additionally on the substrate holder 1 and the cleaning solvent such as ethyl alcohol alone is held inside the liquid supplier 45. Hence, DNA solutions are supplied from the DNA solution plate 9 to the ordinary fluid jet nozzle 2 and the fine fluid jet nozzle 3. The DNA solution plate 9 is obtained by arranging a number of very small pods 9a and the respective pods 9a contain DNA solutions which are different from each other as shown in FIG. 11. The other structures are basically similar to those according to the first embodiment. Hence, the same structure will be simply denoted at the same reference symbols but will not be described.

Figure 12:
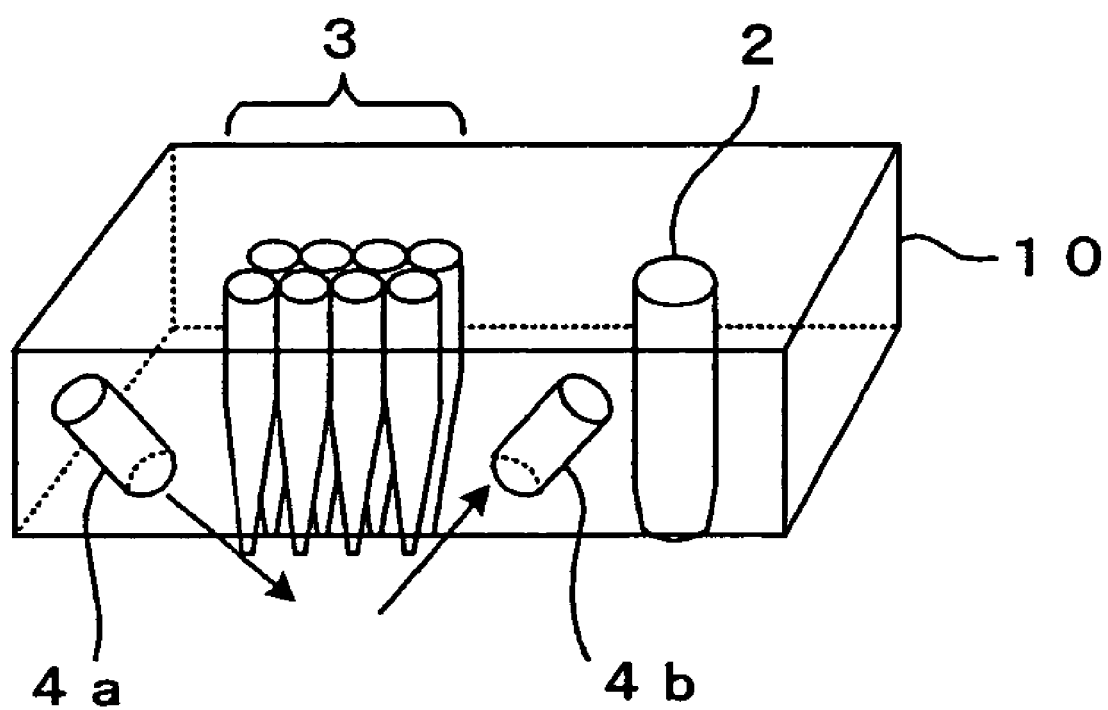
FIG. 12 is a drawing which shows one example of a head for a DNA micro array.

FIG. 12 shows one example of a head of the DNA micro array. The example shown in FIG. 12 is an example that 8-channel fine fluid jet nozzles 3 are disposed. When a multichannel nozzle is used in this manner, the throughput of the apparatus improves. The pitches between the fine fluid jet nozzles 3 coincide with the pitches between the pods 9a of the DNA solution plate 9. The DNA solutions are supplied to the respective nozzles, as the tips of the nozzles are dipped into the DNA solutions which are in the pods 9a. Due to the capillary phenomenon, the DNA solutions are sucked into the tips of the nozzles.

Figure 13:
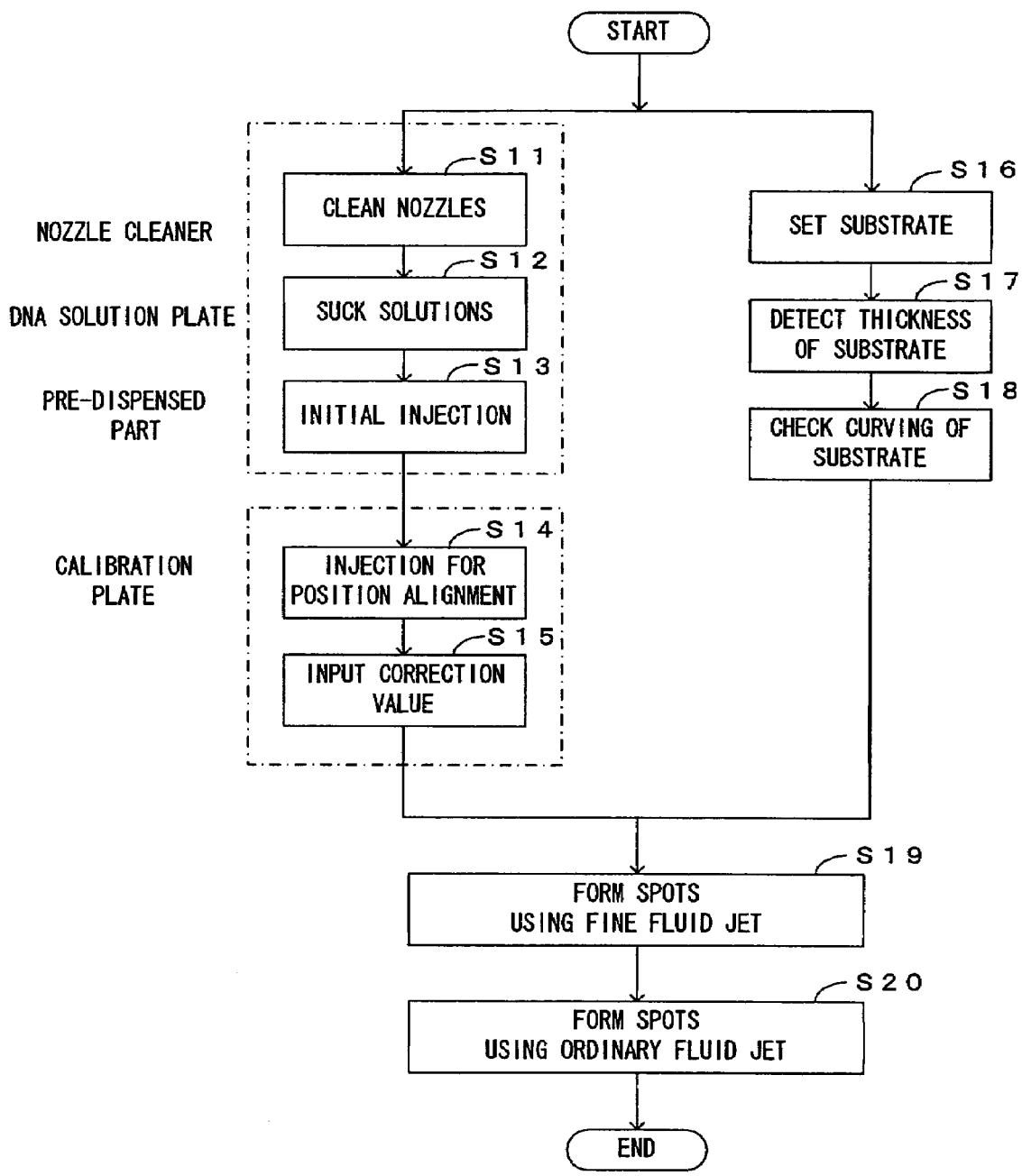
FIG. 13 is a flow chart which shows one example of an operation of the processing apparatus of FIG. 10.

An operation of manufacturing the DNA micro array will now be described. FIG. 13 is a flow chart which shows one example of the operation of the processing apparatus of FIG. 10. Although the basic operation is similar to that shown in the flow chart in FIG. 6, there is a difference that the solutions are supplied from the DNA solution plate 9 to the respective nozzles during manufacturing of the DNA micro array. Noting this, the difference alone will be described and the other aspects will be omitted.

First, as preparation for injection, each nozzle is cleaned in the nozzle cleaner 6 (Step S11). Following this, the head 10 moves to above the DNA solution plate 9, and the tips of the fine fluid jet nozzles 3 are dipped into the DNA solutions which are held in the pods 9a. Due to the capillary phenomenon, the DNA solutions are sucked into the fine fluid jet nozzles 3 (Step S12). In a similar manner, the DNA solution is sucked into the ordinary fluid jet nozzle 2. In the pre-dispensed part 7, each nozzle injects the solution, thereby performing initial injection (Step S13). Since the DNA solutions are supplied to the respective nozzles by means of suction due to the capillary phenomenon, it is necessary to preliminarily inject a required number of times and accordingly remove the DNA solutions which have adhered to the tips of the nozzles. This is because the DNA solutions which have adhered to the tips of the nozzles will have a negative influence which will make it impossible to obtain desired spot diameters if preliminary injection is omitted. Alignment of the respective nozzles relative to each other using the calibration plate 8 (Step S14), input of the correction value (Step S15) and the preparation of the substrate S (Step S16 to Step S18) are similar to those shown in FIG. 6 and therefore will not be described.

When the preparation before forming a pattern is finished, first, spot formation using the fine fluid jet nozzles 3 is executed (Step S19). The head 10 is set to a predetermined position on the substrate S, and drops having the fine particle diameters are supplied upon the substrate S from the fine fluid jet nozzles 3. In consequence, spots having fine diameters (fine spots) are formed on the substrate S. Where the head 10 comprises the 8-channel fine fluid jet nozzles 3, eight spots are formed on the substrate S. One spot is formed as a result of one shot from one fine fluid jet nozzle 3. In the event that plural substrates S are set to the substrate holder 1, eight spots are formed sequentially substrate by substrate.

As for replenishment of the DNA solutions, each DNA solution is replenished to the associated pod 9a. The nozzle tips are then dipped into the DNA solutions which are held in the pods 9a and the DNA solutions are sucked in, whereby the DNA solutions are replenished. After replenishment, preliminary injection is carried out again and spots are then formed. To exchange the DNA solutions, the cleaning solvent is fed under pressure from the liquid supplier 45 and the insides of the nozzles are cleaned within the pre-dispensed part 7 and ultrasonic cleaning using the cleaning solvent is executed within the nozzle cleaner 6. Following this, the nozzle tips are dipped into the new DNA solutions and the DNA solutions are sucked in, whereby the DNA solutions are supplied into the nozzles. These operations are performed simultaneously for the 8-channel fine fluid jet nozzles 3.

After spot formation using the fine fluid jet nozzles 3 has completed, spot formation using the ordinary fluid jet nozzle 2 is executed (Step S20). Spots are created using ordinary fluid jets in a similar fashion to that of creating spots using fine fluid jets. In short, the head 10 is set to a predetermined position on the substrate S, and as drops having the ordinary particle diameters which are larger than the fine particle diameters are supplied onto the substrate S from the ordinary fluid jet nozzle 2, spots having the ordinary diameters (ordinary spots) are formed on the substrate S.

Figure 14A:
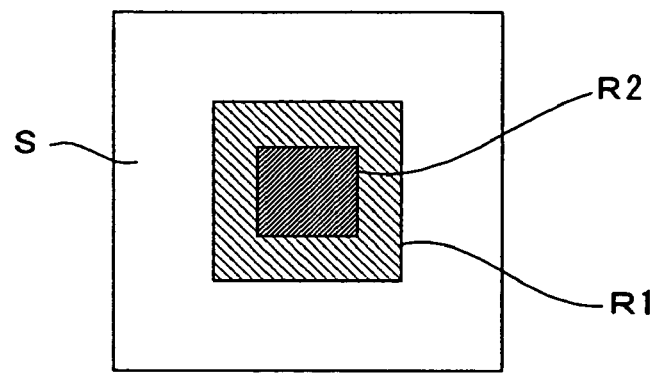
FIG. 14a and FIG. 14b are drawings which show the appearance of a DNA micro array.
Figure 14B:
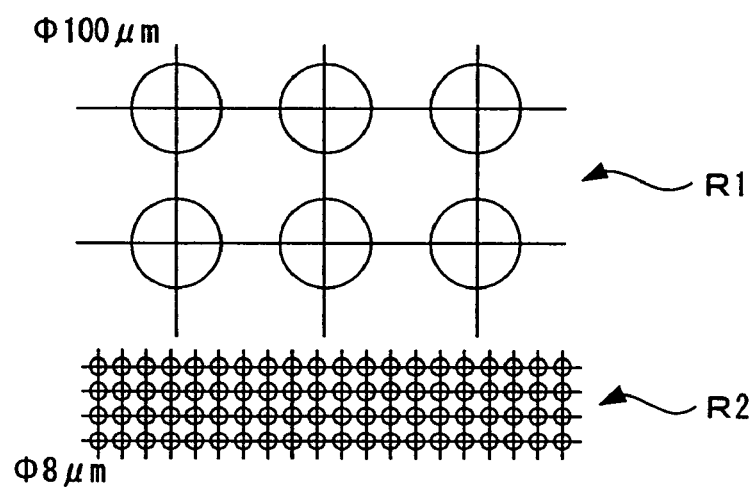

FIG. 14 shows the appearance of a DNA micro array. The section (a) in FIG. 14 represents an example that as a fine region R2, fine spots are formed using the fine fluid jet nozzles 3, and as an ordinary region R1, ordinary spots larger than the fine diameters are formed using the ordinary fluid jet nozzle 2, both on the substrate S of slide glass or the like. Meanwhile, the section (b) in FIG. 14 is an enlarged view of each region. In this example, the fine spot diameters are 8 μm and the ordinary spot diameters are 100 μm.

As described above, in the second embodiment, since drops which have the ordinary particle diameters or the fine particle diameters are supplied onto the substrate S in accordance with the processing region, it is possible to improve the throughput. In other words, while the particle diameters of drops for forming spots having fine diameters need be small diameters when there is only one type of particle diameters of drops, in the event that larger spot diameters than the fine diameters are to be attained with this small particle diameter, the amount of the liquid supplied to the substrate per unit time is restricted, ending up in a deterioration of the throughput. In the second embodiment, since the particle diameters of drops are changed in accordance with the diameters of spots to create, a deterioration of the throughput is prevented. Further, since the solution can be injected in drops having different particle diameters, it is possible to supply drops whose particle diameters are suitable in light of the purpose of analysis, which is highly versatile. Use of the fine fluid jet nozzles 3 in particular realizes injection of drops having such particle diameters which could not have heretofore been stably injected owing to the problem of nozzle clogging and the like in the case of an ink jet nozzle, and therefore, it is possible to reduce the diameters of spots and increase the density of a spot arrangement.

In addition, in the second embodiment, as for DNAs to be mainly analyzed, ordinary spots are arranged using the ordinary fluid jet nozzle 2, and therefore, it is possible to obtain numerically stable results from the analysis. Further, when spot diameters are φ100 μm or larger, the status of a reaction can be visually analyzed at the time of hybridization. On the other hand, since use of the fine fluid jet nozzles 3 achieves injection of drops having such particle diameters which can not be stably injected in the case of an ink jet nozzle, it is possible to arrange fine spots at a high density and improve the efficiency of the analysis. This makes it possible to manufacture a DNA micro array on one substrate even the DNA micro array is to be used for gene analysis on a large scale. Further, since the nozzles are fine, the amount of the adhering solutions are very small even during exchange of the probe DNA solutions, which is advantageous in reducing the problem of cross contamination.

(Chemical Sample Reaction)

Although this embodiment is directed to manufacturing of a DNA micro array on the substrate S, this is not limiting. The invention is applicable also to a chemical sample reaction using a combinatorial chemistry method for instance. In this case, a chemical sample solution plate is used instead of the probe DNA solution plate 9. The pods 9a of the chemical sample solution plate hold chemical sample solutions which contain different components or these components in different proportions.

Figure 15A:
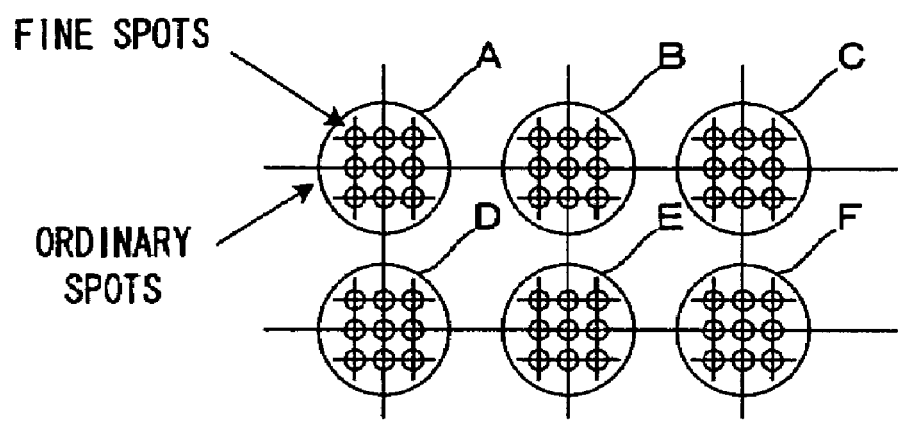
FIG. 15a and FIG. 15b are drawings which show the appearance of a chemical sample reaction.
Figure 15B:
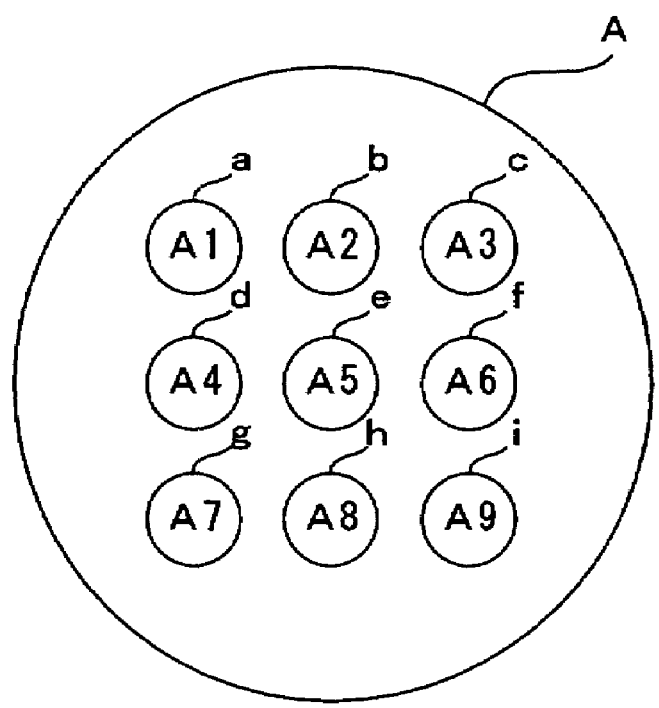

FIG. 15 shows the appearance of a chemical sample reaction. In the section (a) in FIG. 15, nine types of different chemical sample solutions are laid respectively over chemical sample solutions A through F which are different from each other. The section (b) in FIG. 15 is an enlarged view of the chemical sample solution A. From the chemical sample solutions A through F, spots having ordinary diameters (ordinary spots) are formed using the ordinary fluid jet nozzle 2, and from the nine types of different chemical sample solutions a through i, spots having fine diameters (fine spots) are formed using the fine fluid jet nozzles 3. With respect to formation of the spots, after ordinary spots are created first using the ordinary fluid jet nozzle 2, fine spots are then created using the fine fluid jet nozzles 3 respectively over the ordinary spots. In sections where the ordinary spots and the fine spots are laid over each other, chemical reactions occur between the chemical sample solutions which have ordinary particle diameters and the chemical sample solutions which have fine particle diameters. Describing this with reference to the section (b) in FIG. 15, in a spot A1, a chemical reaction (A-a) occurs between the chemical sample solution (A) having the ordinary particle diameters and the chemical sample solution (a) having the fine particle diameters, in a spot A2, a chemical reaction (A-b) occurs between the chemical sample solution (A) having the ordinary particle diameters and the chemical sample solution (b) having the fine particle diameters, and in a spot A3, a chemical reaction (A-c) occurs between the chemical sample solution (A) having the ordinary particle diameters and the chemical sample solution (c) having the fine particle diameters. In this manner, chemical reactions (A-d) through (A-i) occur between the solution (A) and the solutions (d) through (i). The result of these reactions are optically detected, which dramatically improves the efficiency of the experiment.

When the amounts of injection are different due to differences of the properties of various chemical samples, the chemical sample solutions are injected in advance on the calibration plate 8, the different amounts of injection are measured by examining the diameters of spots using a microscope and an injection control signal (spot creating signal) is adjusted in accordance with whether the amounts of injection are sufficient or insufficient, thereby suppressing variations of the amounts of injection.

As described above, since solutions whose drops have two different particle diameters can be injected, it is possible to lay a solution having one particle diameters of drops (fine spots) over a solution having the other particle diameters of drops (ordinary spots). Therefore the apparatus is highly versatile, ensures chemical reactions in a systematic, efficient and prompt manner utilizing combinations of chemical samples, and allows a quick evaluation of the result of the reactions. Since use of the fine fluid jet nozzles 3 in particular realizes injection of drops having such particle diameters which could not have heretofore been stably injected owing to the problem of nozzle clogging and the like in the case of an ink jet nozzle, it is possible to arrange fine spots at a high density over ordinary spots which are formed using the ordinary fluid jet nozzle 2 and dramatically improve the efficiency of the experiment.

Others

The invention is not limited to the embodiments described above but may be modified in various manners in addition to the embodiments above, to the extent not deviating from the object of the invention. For instance, although the embodiments described above require that a feeding position on the substrate S at which a solution is supplied while driving the head 10 in the directions X, Y and Z, any desired drive means may be used as long as the drive means has a structure which moves the head 10 and the substrate S relative to each other three-dimensionally. For example, a feeding position on the substrate S at which a solution is supplied may be controlled with the head 10 fixed and the substrate S driven in the directions X, Y and Z.

Further, although the embodiments described above require that the ordinary fluid jet nozzle 2 and the position of the fine fluid jet nozzle 3 are integrated with each other and driven in a unified manner, a driving mechanism may be disposed for each one of the ordinary fluid jet nozzle 2 and the position of the fine fluid jet nozzle 3 and operated separately.

Further, although the two guide rails 12 and 13 are disposed on the both sides to the substrate holder 1, and therefore, the Y-axes are of the gantry type in that two axes are driven in synchronization to each other according to the embodiments described above, a uni-axis cantilever-like structure comprising one guide rail may be used. When a cantilever-like structure is used, a caution must be exercised as for the mechanical stiffness so that the position accuracy will not deteriorate.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

What is claimed is:

1. A processing apparatus which performs predetermined processing while supplying a processing liquid to a substrate, comprising:

a substrate holder which holds said substrate;

an ordinary fluid jet unit which injects drops of said processing liquid having first particle diameters toward said substrate;

a fine fluid jet unit which injects drops of said processing liquid having fine particle diameters which are smaller than first particle diameters toward said substrate;

a driving device which moves each one of said ordinary fluid jet unit and said fine fluid jet unit relative to said substrate which is held by said substrate holder; and a controller which adjusts the positions of each jet unit relative to said substrate and accordingly controls a feeding position of said drops, wherein said ordinary fluid jet unit comprises: a nozzle body which holds said processing liquid inside and which is capable of injecting drops of said processing liquid from an ordinary outlet which is formed at a tip of said nozzle body; and a pressure applying device which applies a pressure upon said processing liquid which is held in said nozzle body, and application of the pressure by said pressure applying device makes drops injected through said ordinary outlet, and said fine fluid jet unit comprises: a nozzle body which holds said processing liquid inside and which is capable of injecting drops of said processing liquid through a fine outlet which is smaller than said ordinary outlet; and an electrode which is disposed in contact with said processing liquid which is held within said nozzle body, and a voltage is applied upon said electrode with said fine outlet positioned near said substrate, a local electric field is generated in the vicinity of said fine outlet, said processing liquid near said fine outlet is charged, and thus charged drops of said processing liquid are injected through said fine outlet.

2. The processing apparatus of claim 1, wherein said driving device moves said ordinary fluid jet unit and said fine fluid jet unit in a unified manner relative to said substrate.

3. The processing apparatus of claim 1, comprising plural such ordinary fluid jet units.

4. The processing apparatus of claim 1, comprising plural such fine fluid jet units.

5. The processing apparatus of claim 1, wherein said driving device comprises an X-axis drive portion which moves said ordinary fluid jet unit and said fine fluid jet unit relative to said substrate in an X-axis direction which is the direction of any desired one axis which is approximately parallel to said substrate, a Y-axis drive portion which moves said ordinary fluid jet unit and said fine fluid jet unit relative to said substrate approximately parallel to said substrate and in a Y-axis direction which is orthogonal to said X-axis direction, a Z-axis drive portion which moves said ordinary fluid jet unit and said fine fluid jet unit relative to said substrate in a Z-axis direction which is orthogonal to said X-axis direction and said Y-axis direction, and as said Z-axis drive portion is operated, the gap between said fine fluid jet unit and said substrate is finely adjusted.

6. The processing apparatus of claim 5, further comprising a non-contact displacement sensor which detects a displacement of the gap between said fine fluid jet unit and said substrate in a non-contact fashion, and as said Z-axis drive portion is operated in response to a displacement signal from said non-contact displacement sensor, the gap between said fine fluid jet unit and said substrate is finely adjusted.

7. The processing apparatus of claim 6, wherein said non-contact displacement sensor is a regular reflection laser displacement gauge which comprises a light projector which projects laser toward said substrate and a light receiver which receives reflected laser light which is reflected from said substrate.

8. The processing apparatus of claim 6, wherein said non-contact displacement sensor continuously detects an unsupplied region which is free from said drops and does not include a feeding position at which said drops are supplied to said substrate from said fine fluid jet unit.

9. The processing apparatus of claim 8, further comprising a position adjusting mechanism which adjusts a detect position of said non-contact displacement sensor so as to detect any desired position in the vicinity of said feeding position at which said drops are supplied from said fine fluid jet unit.

10. The processing apparatus of claim 6, wherein said non-contact displacement sensor detects an area in the vicinity including a feeding position at which said drops are supplied to said substrate from said fine fluid jet unit before said fine fluid jet unit supplies said drops to said substrate, and then stops detecting.

11. The processing apparatus of claim 10, further comprising a position adjusting mechanism which adjusts a detect position of said non-contact displacement sensor so as to detect any desired position in the vicinity of said feeding position at which said drops are supplied from said fine fluid jet unit.

12. The processing apparatus of claim 1, further comprising a calibration plate which adjusts the positions of said ordinary fluid jet unit and said fine fluid jet unit relative to each other.

13. The processing apparatus of claim 1, wherein said ordinary fluid jet unit and said fine fluid jet unit inject a colloid solution of fine metal particles as said processing liquid toward said substrate.

14. The processing apparatus of claim 13, wherein said substrate can mount integrated circuit components, and fine patterns having fine widths in regions such as peripheral regions of said integrated circuit components are formed on said substrate as drops of said processing liquid having said fine particle diameters are injected from said fine fluid jet unit, whereas ordinary patterns having ordinary widths which are wider than said fine widths are formed on said substrate as drops of said processing liquid having said first particle diameters are injected from said ordinary fluid jet unit.

15. The processing apparatus of claim 1, wherein said ordinary fluid jet unit and said fine fluid jet unit inject a soluble derivative of conductive polymers as said processing liquid toward said substrate.

16. The processing apparatus of claim 1, wherein said processing liquid is a conductive solution and wherein said substrate is a multi-layer substrate, as drops of a conductive solution which have said first particle diameters is injected from said ordinary fluid jet unit, through holes which is formed on said multi-layer substrate and which have ordinary diameters are filled up, as drops of a conductive solution which have said fine particle diameters is injected from said fine fluid jet unit, through holes which is formed on said multi-layer substrate and which have fine diameters which are smaller than said ordinary diameters are filled up.

17. The processing apparatus of claim 1, wherein solder bumps having ordinary diameters are formed on said substrate as said ordinary fluid jet unit injects drops which have said first particle diameters, whereas solder bumps having fine diameters which are smaller than said ordinary diameters are formed on said substrate as said fine fluid jet unit injects drops which have said fine particle diameters.

18. The processing apparatus of claim 1, wherein said processing liquid is a DNA solution, as a DNA solution having said first particle diameters is injected from said ordinary fluid jet unit, a DNA micro array in which plural spots having ordinary diameters are arranged is formed on said substrate, and as a DNA solution having said fine particle diameters is injected from said fine fluid jet unit, a DNA micro array in which plural spots having fine diameters which are smaller than said ordinary diameters are arranged is formed on said substrate.

19. The processing apparatus of claim 1, wherein said processing liquid is a chemical sample solution, as a chemical sample solution having said first particle diameters is injected from said ordinary fluid jet unit, a micro array in which plural spots having ordinary diameters are arranged is formed on said substrate, as a chemical sample solution having said fine particle diameters is injected from said fine fluid jet unit, a micro array in which plural spots having fine diameters which are smaller than said diameters are arranged is formed respectively over said spots having said ordinary diameters, and chemical reactions are accordingly caused between said chemical sample solution having said first particle diameters and said chemical sample solution having said fine particle diameters.

* * * * *